United States Patent [19]

Pelanek et al.

[11] Patent Number: 5,089,389
[45] Date of Patent: Feb. 18, 1992

[54] BUFFERED COMPOSITION, COATED ARTICLE TEST DEVICE AND A METHOD FOR THEIR USE

[75] Inventors: Geraldine A. Pelanek, Webster; Robert W. Zercie, Rochester; James D. Kanaley, Honeoye Falls, all of N.Y.

[73] Assignee: Eastman Kodak Company, Rochester, N.Y.

[21] Appl. No.: 398,565

[22] Filed: Aug. 25, 1989

[51] Int. Cl.⁵ .................. G01N 35/571; C12Q 1/00
[52] U.S. Cl. ............................. 435/7.36; 435/7.92; 435/29; 435/180; 435/243; 435/871
[58] Field of Search ............... 435/7.36, 7.9, 7.92, 435/7.95, 810, 970, 975, 29, 291; 436/518, 511, 531, 541; 422/56, 61, 68, 69

[56] References Cited

U.S. PATENT DOCUMENTS

| | | | |
|---|---|---|---|
| 4,241,045 | 12/1980 | Gaafar | 424/1 |
| 4,497,899 | 2/1985 | Armstrong et al. | 436/510 |
| 4,497,900 | 2/1985 | Abram et al. | 436/511 |
| 4,803,159 | 2/1989 | Smith-Lewis | 435/26 |
| 4,847,199 | 7/1989 | Snyder et al. | 435/36 |
| 4,981,786 | 1/1991 | Dafforn et al. | 422/56 |

FOREIGN PATENT DOCUMENTS 89-00695 1/1989 World Int. Prop. O. .

*Primary Examiner*—Esther L. Kepplinger
*Assistant Examiner*—Carol E. Bidwell
*Attorney, Agent, or Firm*—J. Lanny Tucker

[57] ABSTRACT

A buffered composition includes whole chlamydial or gonococcal organisms or an antigen thereof, and a nonionic fluorinated surfactant in an amount of at least about 0.05 weigh percent. This composition is useful in a positive control test used in diagnostic assays for chlamydial or gonococcal organisms. It is particularly useful when coated in an article used in such assays, such as disposable test devices having nonionic polyamide filtration membranes in the bottom of test wells.

18 Claims, 1 Drawing Sheet

BUFFERED COMPOSITION, COATED ARTICLE TEST DEVICE AND A METHOD FOR THEIR USE

FIELD OF THE INVENTION

The present invention relates to a buffered composition, an article upon which it can be coated, and a diagnostic method for the determination of chlamydial or gonococcal organisms or antigens.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, long-keeping, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more serotypes of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population since it is believed that there are millions of cases each year of nongonococcal urethritis alone.

Gonorrhea is a disease usually transmitted by sexual contact caused by a bacterium of the Neisseria genus, especially *N. gonorrheae*. The disease has plagued mankind for thousands of years, and although antibiotics have helped control its spread, it still persists in epidemic proportions in many parts of the world. The importance of detection and treatment of this disease is well recognized. *N. meningitidis* and *N. lactamica* are also species of considerable medical and diagnostic interest.

Because of the widespread nature of these diseases, there is considerable interest in having a rapid, simple and reliable test for detection of chlamydial and gonococcal organisms. Assays for *C. trachomatis* and *N. gonorrheae* carried out using a solid support are described in U.S. Pat. Nos. 4,497,899 (issued Feb. 5, 1985 to Armstrong et al) and 4,497,900 (issued Feb. 5, 1985 to Abram et al). The described assays are performed by extracting antigen from the organism and coating it on a bare solid support. The coated antigen is then detected with either one or two antibodies, one of which is suitably labeled. The critical feature of the assays appears to be the use of a solid support for attachment which is untreated or uncoated with any material. Attachment of antigen is apparently achieved by incubating the coated support for an extended time sufficient to cause adsorption of antigen thereon. The entire assay described in U.S. Pat. No. 4,497,899 takes at least 3 hours to perform.

A much more rapid test for chlamydial or gonococcal organisms which has high reliability and can be performed at room temperature is described and claimed in U.S. Ser. No. 255,923 (filed on Oct. 7, 1988 by Pronovost). Our colleague found that ionically charged (specifically cationic) supports attract chlamydial or gonococcal antigen and enable one to quickly and sensitively detect the antigen.

A further improvement is described in U.S. Ser. No. 255,920 (filed Oct. 7, 1988 by Mauck and issued July 16, 1991 as U.S. Pat. No. 5,032,504) which describes the use of a surfactant-coated uncharged membrane in chlamydial assays. That invention enables one to rapidly and sensitively detect the antigen in biological specimens that contain copious amounts Of whole blood, mucus or components thereof.

Still another advance is described in U.S. Ser. No. 366,100 (filed June 14, 1989 by Mauck et al) in which chlamydial antigen is detected in an assay using a microporous filtration membrane having surface hydroxy groups. Such membranes exhibit increased keeping properties and thus provide significant marketing and user advantages.

The current product marketed by Kodak as the SURECELL TM Chlamydia Test Kit has been received by the marketplace quite positively. One of the reasons for this is the presence of positive and negative controls within the test device used for the assay. This device contains a surfactant-coated BIODYNE TM polyamide membrane like that described in U.S. Ser. No. 255,920 (noted above) in the test wells used for both the controls and assay of the unknown. This membrane is nonionic and has no hydroxy or ionic groups on its surface.

It was found in manufacturing this test kit that frequently the positive control well did not have adequate and uniform coverage of reagents when they were deposited using automated equipment. Particularly, antigen placed within the positive control well was not uniformly distributed on the membrane unless deposition was carefully done by hand using large volumes of fluid. It was thus desirable to find a way to rapidly and uniformly incorporate the needed reagents in the positive control well using automated means and without large volumes of fluid.

SUMMARY OF THE INVENTION

The problems noted above were overcome using as a reagent composition for the positive control, a buffered composition comprising whole chlamydial or gonococcal organisms or an extracted antigen thereof, and a nonionic fluorinated surfactant in an amount of at least about 0.05 weight percent.

Further, this invention provides an article comprising a water-insoluble substrate having coated thereon a buffered composition comprising whole chlamydial or gonococcal organisms or an extracted antigen thereof, and a nonionic fluorinated surfactant in an amount of at least about 0.05 weight percent.

A method for the determination of a chlamydial or gonococcal antigen in a disposable test device while simultaneously providing a positive control test comprises the steps of:

A. adding an aqueous solution containing unknown amounts of a chlamydial or gonococcal antigen extracted from a biological specimen suspected of containing chlamydial or gonococcal organisms, respectively, to at least two test wells of a disposable test device, the test wells having nonionic polyamide microporous membranes located at the bottom thereof, a first test well being suited for determination of the unknown antigen, a second test well being suited as a positive control by having coated therein a buffered composition comprising whole chlamydial or gonococcal organisms or an extracted antigen thereof, respectively, and a nonionic fluorinated surfactant in an amount of at least about 0.05 weight percent,
to bind both unknown and control antigen to the respective membranes, B. contacting chlamydial or gonococcal antigen bound to the membrane in each test well with chlamydial or gonococcal antibody, respectively, so as to form an immunological complex on the membranes, and C. detecting the presence of complex on the membrane in the first test well as an indication of the presence of unknown chlamydial or gonococcal organisms in the biological specimen, and the presence of complex on the membrane in the second test well as a positive control.

The assay of this invention is rapid, reliable and simple to use. Generally, it can be carried out in less than 25 minutes at room temperature if desired. It is highly reliable for detecting extracted chlamydial or gonococcal antigen, and particularly the lipopolysaccharide antigen extracted from *Chlamydia trachomatis*.

The present invention achieves additional advantages in manufacturability because the particular buffered composition used in the positive control test of the assay can be rapidly and uniformly deposited on the nonionic membranes of the test device. This composition can be deposited using automated equipment without concern for nonuniform coverage of the membrane and attending nonuniform dye formation during the assay. Moreover, minimal fluid is needed for deposition of the composition. The presence of certain levels of nonionic fluorinated surfactant in the composition provides these desirable results.

DETAILED DESCRIPTION OF THE INVENTION

Figure 1:
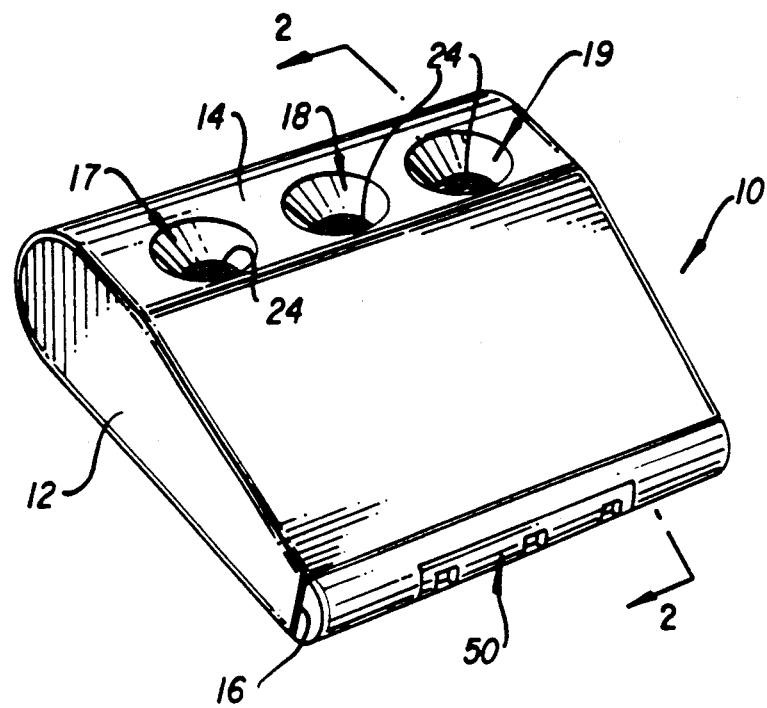
FIG. 1 is a perspective illustration of a representative disposable test device useful in the practice of the present invention having three test wells at the bottom of which is a nonionic microporous filtration membrane.

The present invention comprises a method for determining the presence of *C. trachomatis* (or other chlamydial species) or *N. gonorrheae* (or other gonococcal species) in a biological specimen which has been obtained from a patient using any suitable medical or diagnostic techniques. Such specimens include, for example, swab specimens obtained from the cervix, urethra, throat, eye or anus of a patient, and body fluids such as synovial fluid or fluid from lesions. The biological specimens so obtained are suspected of containing bacterial organisms which comprise the chlamydial or gonococcal antigen (or mixture thereof) to be determined. The specimens are particularly likely to contain whole blood or mucus, and sometimes large amounts of both.

While the assay can be carried out to detect antigens from intact chlamydial or gonococcal organisms, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in EP-A-0 183 383 (published June 4, 1986). The use of anionic detergents or salts such as sodium dodecyl sulfate and deoxycholate is described in U.S. Pat. Nos. 4,497,899, 4,497,900 (both noted above) and 4,663,291 (issued May 5, 1987 to Rose).

In a preferred embodiment, the present invention can be used to detect the chlamydial lipopolysaccharide (glycolipid group) antigen (as described, for example, in EP-A-0 193 431, published Sept. 3, 1986). Extraction procedures are also described therein. In another embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using the present invention.

A preferred extraction composition is described in detail below in connection with the examples. The central feature of that composition is the presence of an alcoholamine or salt thereof and its high pH.

In addition, it may be desirable to use a protease in the extraction procedure to break down whole blood and mucus. A useful protease is described below in relation to the examples.

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container, including devices specially designed for extraction of antigen. Useful devices are known in the art, including U.S. Pat. No. 4,746,614 (issued May 24, 1988 to Devaney, Jr. et al).

Extracted antigen is contacted with a nonionic polymeric microporous membrane having an average pore size of from about 1 to about 10 μmeters, and preferably of about 5 μmeter. The membrane is prepared from a polyamide, that is a long-chain synthetic polymer having recurring amide groups in the polymer backbone. They are generally copolymers of a diamine and a dicarboxylic acid, or homopolymers of a lactam of an amino acid. Representative materials include, but are not limited to, polyhexamethylene dodecanediamide (nylon 612), polyhexamethylene adipamide (nylon 66), poly-ε-caprolactam (nylon 6), polyhexamethylene sebacamide (nylon 610) and poly-7-aminoheptanoamide (nylon 7), and mixtures thereof. Polyhexamethylene adipamide (nylon 66) is preferred Unlike some of the membranes known in the art, the membrane used herein is a nonionic membrane, and does not have pendant hydroxy groups. One such membrane is commercially available from Pall Corp. under the mark BIODYNE TM A microporous membranes.

Examples of other membranes and teaching of details about making them are provided in EP-A-0 173 500 (published Mar. 5, 1986).

In the practice of this invention, the membrane can be further treated by coating with a suitable nonionic surfactant, as described for example in U.S. Ser. No. 255,920 (noted above).

The membrane described herein can be used in combination with other equipment (bottles, test tubes, swabs, beakers or cups) in order carry out the assay. Alternatively and preferably, it is fitted into a disposable test device in which the assay can be carried out and all fluids accommodated. Useful configurations of test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May, 1984 to Liotta). Particularly useful devices are described and claimed in U.S. Ser. No. 240,179 (filed Sept. 6, 1988 by Hinckley et al and issued May 1, 1990 as U.S. Pat. No. 4,921,677), and U.S. Pat. No. 4,833,087 (issued May 23, 1989 to Hinckley).

The contact is carried out for a time sufficient for antigen to bind directly with the membrane. Generally, almost immediately upon contact of the antigen with the membrane, the antigen is bound thereto. The antigen is preferentially bound to the membrane as opposed to other proteins, cell components, whole blood or mucus or other debris which may be present in the test specimen or reagents used in the assay.

Generally within about 10 minutes, and preferably within 1 to 5 minutes, of the contact, the bound antigen is contacted with a reactive composition comprising a chlamydial of gonococcal antibody so as to form an immunological complex bound to the support. Fluid and unbound materials may be removed quickly at the same time. Fluid and unbound materials (such as whole blood and mucus components) in the specimen are allowed to flow through the membrane and collected in a suitable compartment during the time the antigen is bound to the membrane.

The antibody used in this assay is specifically immunoreactive with one or more chlamydial or gonococcal serotypes (depending upon what organism is of interest). It can be polyclonal or monoclonal. If polyclonal, it is commercially available or prepared in various animals using known techniques employing an antigen common to the strain of organism to be detected. A single antibody or mixture thereof can be used. For example, antibody to either the chlamydial lipopolysaccharide or major outer membrane protein antigen, or antibodies to both antigens can be used in the assay. Preferably, the antibodies are monoclonal which are either commercially available or prepared using standard hybridoma technology. Useful procedures for preparing antibodies are described, for example, in EP-A-0 193 431 and U.S. Pat. No. 4,427,782 (noted above).

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent moieties, chemiluminescent moieties, phosphorescent moieties, biotin or its derivatives, avidin or its derivatives, ferritin, magnetizable particles, dyed particles, gold sols, dye sols, colored *Staphylococcus aureus* cells and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example; if the label is biotin, it can be reacted with avidin which is conjugated with an enzyme to provide a detectable species. Where the label is an enzyme, such as glucose oxidase, urease, peroxidase, alkaline phosphatase and others, a composition capable of providing a dye in the presence of the enzyme is also needed.

In a particularly preferred embodiment, the label is peroxidase, and at some point in the assay, hydrogen peroxide and a suitable dye-providing composition is added to provide a detectable dye. For example, useful dye-providing reagents include leuco dyes, such as triarylimidazole leuco dyes (as described in U.S. Pat. Nos. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a preferred embodiment, the chlamydial or gonococcal antibody is not labeled, and detection cf the antibody-antigen complex formed and bound to the membrane is accomplished using a second antibody (that is, an anti-antibody) which is specific to the unlabeled antibody and is appropriately labeled. This second antibody can be polyclonal or monoclonal and obtained from various sources or prepared using known procedures.

Once the bound antigen has been contacted with the chlamydial or gonococcal antibody, a bound immunological complex is formed on the membrane. To hasten the formation of this complex, the antibody and antigen are generally incubated at a temperature of from about 15° to about 30° C. for up to 10 minutes. Preferably, the incubation is carried out at from about 18° to about 25° C. (that is, room temperature) for from 1 to 5 minutes.

After the incubation and generally within about 10 minutes of the antibody-antigen contact, the bound complex is washed one or more times with a wash solution which generally has a pH of from about 7 to about 12. The solution preferably contains one or more surfactants to aid in separating unbound materials from the bound complex. Particularly useful surfactants are cationic surfactants, as described in relation to the examples below.

In the embodiment described above where the chlamydial or gonococcal antibody is labeled, the assay procedure after washing is to detect the label directly or indirectly after addition of the appropriate reagents. This is done relatively quickly after washing the bound complex, that is generally within about ten minutes, and preferably within about one to about five minutes. If desired, label detection can be hastened with incubation if the reagents warrant it. The label is then detected using standard equipment and procedures.

After this contact, the resulting antigen-antibody-antibody complex which is bound to the coated membrane is incubated generally for up to about ten minutes at a temperature of from about 15° to about 30° C., and preferably for about one to about five minutes at from 18° to 25° C.

Further washing is carried out to remove uncomplexed materials, and suitable enzyme substrates or other needed reagents are added to provide a detectable species. The bound antigen-antibody-labeled antibody complex is then detected on the membrane using standard radiometric, colorimetric, fluorescent or other detection techniques.

A diagnostic test kit can be used to supply the disposable test device and one or more other component compositions, solutions or equipment needed for carrying out the assay.

In the method for chlamydial or gonococcal determination described above, the advantage presented by the present invention is the use of a particular composition for a positive control. This composition comprises whole chlamydial or gonococcal organisms, or antigens extracted therefrom. Whole organisms can be obtained from cultures, or from commercial sources. Preferably, extracted antigens are used. An important feature of the composition is the presence of at least about 0.05, and preferably from about 0.1 to about 0.5, weight percent of a nonionic fluorinated surfactant.

A number of useful surfactants can be used, alone or in admixture, in the composition as long as they are nonionic and do not adversely affect the assay. Especially useful surfactants are the perfluoroalkylpolyoxyethylenes, fluorinated alkyl alkoxylates and fluorinated alkyl ester compounds. These are commercially available under as ZONYL ™ (DuPont) and FLUORAD ™ (3M Company), such as ZONYL ™ FSN and ZONYL ™ FSN-100, and FLUORAD ™ FC-170-C, FLUORAD ™ FC-170, FLUORAD ™ FC-430, FLUORAD ™ FC-431 and FLUORAD ™ FA-740. Other useful surfactants which are commercially available can be readily discovered by consulting *McCutcheon's Emulsifiers and Detergents* North American Edition, McCutcheon Division, Publishing Co., Glen Rock, N.J., 1988.

Particularly useful surfactants are the perfluoroalkylpolyoxyethylene derivatives having from 8 to 14 oxyethylene groups and from 3 to 8 perfluoroalkyl groups, such as ZONYL ™ FSN and ZONYL ™ FSN. ZONYL ™ FSN is most preferred.

The buffered composition contains one or more buffers, either organic or inorganic, to provide or maintain a pH of from about 6 to about 9. The amount of buffer would be readily apparent to one of ordinary skill in the art.

Optionally, the buffered composition can include a fluorescent dye which does not interfere with detection of the antigen in the positive control, but which dye may aid in manufacturing techniques. One such dye is fluorescein disodium salt dihydrate (available from Kodak Laboratory and Research Products), but others would be readily apparent to one skilled in the art.

Moreover, the composition can also optionally include one or more preservatives (such as merthiolate) or one or more proteins, such as bovine serum albumin, fetal calf serum albumin, human serum albumin and ovalbumin.

The composition can be mixed in the buffer and kept in solution until use, but preferably it is coated on a water-insoluble substrate of some type for later use. Useful substrates include test tubes, microtiter places, glass or polymeric films, cuvettes, pipettes and other devices or articles known in the art. The composition is applied to the substrate in any suitable fashion and then dried, and optionally packaged for storage or sale.

Figure 2:
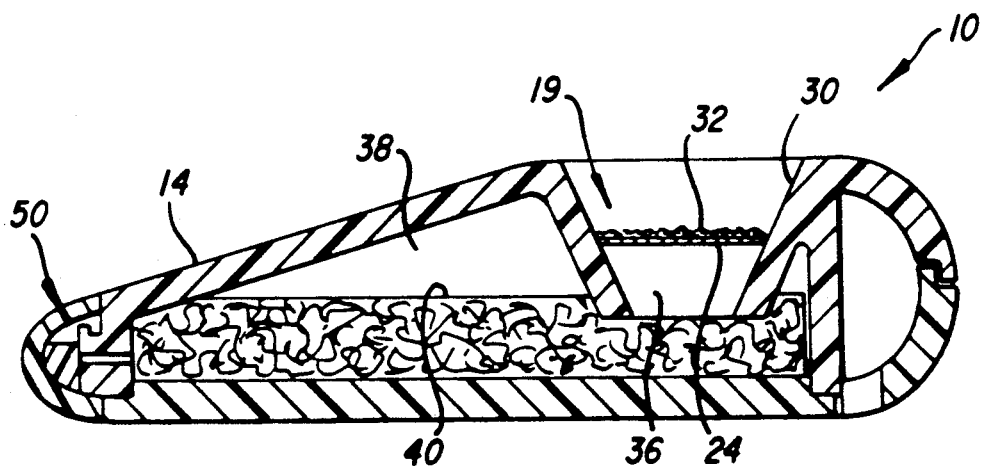
FIG. 2 is a cross-sectional view of the test device of FIG. 1 showing a membrane at the bottom of a test well and a dried coating of the buffered composition of this invention on the membrane.

A preferred article is a disposable test device like those described herein and in the references noted above. This test device can have any of a number of configurations, but a preferred embodiment is shown in FIGS. 1 and 2. Thus, test device 10 has water-insoluble frame 12 having top surface 14 and front edge 16. Mounted on edge 16 is a slide valve 50 for preventing or allowing drainage of fluids from the three test wells 17, 18 and 19 located in top surface 14. At the bottom of each of test wells 17, 18 and 19 is mounted a nonionic polyamide microporous membrane 24 (largely obscured) through which uncomplexed materials flow while the complex formed between antigen and antibody is retained on the membrane.

FIG. 2 shows test device 10 and test well 19 in cross-section. Test well 19 contains side wall 30 and microporous membrane 24 upon which buffered composition 32 has been coated. Membrane 24 is mounted in the test well over compartment 36 which is connected to lower compartment 38 containing absorbent 40 for absorbing fluid drained through the membrane. When a sample of extracted antigen is added to test well 19, the extracted antigen and the buffered composition 32 form an immunological complex on membrane 24 for detection as a positive control.

Preferably, in the method generally described above, the extracted antigen solution is added to three test wells of a disposable test device. One of the wells is for the determination of unknown amounts of antigen. A second well is used for the positive control and an optional third well is used as a negative control. The dried buffered composition is located on a side wall or membrane of the well used as the positive control. Preferably, it is coated on the membrane.

In all wells containing antigen (either known or unknown), the antigen binds to the membranes and forms an immunological complex thereon when chlamydial or gonococcal antibody is added to the wells. This complex is detected using the procedures described above. The presence of a detectable signal in the positive control well aids in indicating that the assay was carried out properly, the assay reagents are working properly and the test device is functioning properly.

The following examples are provided to illustrate, but not limit the scope of, the present invention.

Materials:

SURECELL ™ test devices used in the assays contained 5 $\mu$meter microporous filtration membranes available from Pall Corp. The devices used in the assays of the invention contained BIODYNE ™ A membranes which had been coated with ZONYL ™ FSN nonionic surfactant. These membranes were located at the bottom of the three test wells of the devices.

The prefilter used was a 10 $\mu$meter HDC filter available from Pall Corp.

An extraction device like that described in U.S. Pat. No. 4,746,614 (noted above) was used. It contained two separate dried coatings of: (1) tris(hydroxymethyl)aminomethane buffer (from 20 $\mu$l of a 1.65 molar solution, pH 11.1) with thimerosal preservative (0.01 weight %), and (2) a mixture of dithiothreitol (0.188 molar) from a solution (50 $\mu$l of 2-(N-morpholino)ethanesulfonic acid buffer (10 mmolar, pH 6), sodium azide (1.54 mmolar), ethylenediamine tetraacetic acid (5.4 mmolar) dimedone (21.4 mmolar) and poly(acrylamide)(6.35 weight %).

The extraction composition comprised ethanolamine hydrochloride (0.47 molar), sodium chloride (0.27 molar), disodium ethylenediaminetetraacetic acid (45 mmolar , EMCOL ™ CC-36 cationic surfactant (0.45 weight % from 10% solution in methanol, quaternary ammonium chlorides of polypropoxy-t-amine mixture from Witco Chemical), sodium azide (0.027 molar) and sodium hydroxide (0.66 molar) to obtain a final pH of 13.

The mouse monoclonal antibody to the chlamydial lipopolysaccharide was prepared using standard hybridoma technology and a mouse cell line and stored in a solution of phosphate buffered saline solution (pH 7.2) containing sodium azide (0.01 weight %). An antibody reagent composition was prepared by adding a sample (19 μl of the antibody solution to a phosphate buffered saline solution (diluting 1:800) containing casein (0.5 weight %) as a blocking protein and LONZAINE TM C amphoteric surfactant (0.01 weight %, available from Lonza Co.), and 0.01% merthiolate as an antimicrobial agent, then filtered through a 0.22 μmeter filter to obtain a working solution.

The labeled polyclonal antibody used was a goat anti-mouse IgG antibody conjugated to horseradish peroxidase (obtained from Bio-Rad). This conjugate was diluted to about 1:1000 in a phosphate buffered saline solution containing casein (0.5 weight %) and LONZAINE TM C amphoteric surfactant (0.01 weight %), 4'-hydroxyacetanilide (10 mmolar) and merthiolate (0.01 weight %) then filtered through a 0.22 μmeter filter to obtain a working solution.

A negative control reagent solution was made up of creatine kinase-MB antibody (5 μg/ml), casein (0.5 weight %), LONZAINE TM C amphoteric surfactant (0.01 weight %) and preservative (0.01 weight %) in phosphate buffered saline solution (pH 7.2).

A protease solution contained AMIDECK TM protease (4 mg/ml, 170 units/mg, available from BioProducts Division, Eastman Kodak Co.) in 2-(N-morpholino)ethane sulfonic acid buffer (10 mmolar, pH 6), sodium chloride (50 mmolar), calcium chloride (5 mmolar), 1,2-propanediol (10% w/v) and preservative (0.01 weight %).

Another solution contained hydrogen peroxide (12 weight % in water), diethylenetriaminepentaacetic acid (10 μmolar) and preservative (0.01 weight %).

A wash solution comprised 3-cyclohexyl-amino-2-hydroxy-1-propanesulfonic acid buffer (0.05 molar, pH 10), EMCOL TM CC-9 cationic surfactant (0.75 weight %) and preservative (0.01 weight %).

A dye-providing composition 2-(4-hydroxy-3-methoxyphenyl)-4,5-bis(4-methoxyphenyl)imidazole leuco dye (0.008 weight %), poly(vinyl pyrrolidone) (1 weight %), sodium phosphate (10 mmolar, pH 6.8) diethylenetriaminepentaacetic acid (10 μmolar), 4'-hydroxyacetanilide (2 mmolar) and hydrogen peroxide (10 mmolar).

EXAMPLE 1

Buffered Composition for Positive Control in Assay for Chlamydial Antigen

A buffered composition of this invention was prepared as follows:

A 150-ml flask was charged with 93.1 ml of a sodium hydroxide solution (0.1 normal) and chlamydial serovar J inactivated purified elementary bodies, diluted with bovine serum albumin in phosphate buffered saline solution (0.1 mg/ml, pH 7.2), was added. The concentration of elementary bodies added to the flask was $1.66 \times 10^7$ pg/ml. The solution was mixed for about ten seconds and then allowed to stand for five minutes to completely extract the antigen. Citric acid (2 molar, about 2 ml) was then titrated into the extraction solution to neutralize the solution to pH 7.0. Final citrate concentration was 38 mmolar. Bovine serum albumin (1 ml of a 10% solution in phosphate buffered saline solution) was added and mixed. The final albumin concentration was 0.1%. ZONYL TM FSN (2.5 ml of a 5 weight % solution in nanopure grade water) was added and mixed. The final ZONYL TM FSN concentration was 0.125%. Sodium azide (100 μl of a 10 weight % solution in nanopure water) was added and mixed. The final azide concentration was 0.01 weight %. The fluorescein dye (100 μl of a 5 weight % solution in nanopure water) was added and mixed providing a final dye concentration of 0.005 weight %. This buffered composition solution was kept at 4° C.

The final antigen concentration was 6500 Pg/30 μl of solution, which was the amount that was added to a positive control well of a disposable test device as described herein, allowed to flow through the microporous membrane therein, then air dried at room temperature on the membrane for 15–30 minutes.

EXAMPLE 2

Assay for Chlamydial Antigen Using Buffered Composition as Positive Control

This example illustrates the use of the buffered composition from Example 1 as a positive control composition in an assay for inclusion conjunctivitis (a disease caused by *Chlamydia trachomatis*). Ocular swabs from newborn infants, born to mothers suspected of being infected with this organism, were used as the source of antigen.

The protease solution (280 μl) was added to extraction devices (described above), followed by addition of the swab samples. The swabs were swirled in the solution for ten seconds and then allowed to set for three minutes at room temperature. The extraction composition (280 μl was added to the extraction devices, the swab was swirled for ten seconds and allowed to set for three minutes at room temperature. The hydrogen peroxide solution (280 μl) was added to the devices, the swab was again swirled for ten seconds, then allowed to incubate for three minutes.

The resulting solution containing extracted antigen was removed using a pipette and prefiltered into the test wells of the test device (200 μl per well). The wells were washed twice with the wash solution (about 160 μl each time) and the anti-chlamydial antibody composition (80 μl) was added to the sample and positive control wells only, while the negative control reagent (80 solution μl) was added to the negative control well only. After two minutes incubation at room temperature, the wells were washed twice with the wash solution (about 160 μl each). Then the labeled antibody composition (80 μl) was added to each well followed by five minutes incubation at room temperature.

After washing each well twice again, the dye-providing composition (80 μl) was added to each well, followed by incubation at room temperature for five minutes. The dye on the membrane in the wells were visually graded 0 to 10 (0 for no dye and 10 being highest dye density). The negative control well showed a score of 1 while the sample and positive control wells both showed scores of 9 or 10. These results were confirmed by standard culture and direct fluorescent antibody assay procedures.

EXAMPLE 3

Comparison of Surfactant Amounts in Buffered Composition Used for Positive Control This example compares surfactant amounts in the buffered composition used for the positive control.

Buffered compositions were prepared containing different concentrations of ZONYL TM FSN surfactant, added to the positive control wells and dried, as described in Example 1. Both surfactant coated and uncoated membranes were tested. Test wells containing these membranes (in test devices) were used in an assay for chlamydia as described in Example 2. The dye observed in the positive control wells was visually graded from 0 to 10, with 7 being the desired score. The results, shown in the following Table, are the average of 16 tests.

TABLE

| Surfactant Concentration (%) in Buffered Composition | Biodyne A Membrane | Test: Visual Score | No. of Tests Giving Incomplete Signal[1] | Spot Quality |
| --- | --- | --- | --- | --- |
| 0.025 | uncoated | 7–8 | 7 | acceptable |
|  | surfactant coated[2] | 7–8 | 10 | acceptable |
| 0.100 | uncoated | 7 | 1 | acceptable |
|  | surfactant coated | 7 | 0 | acceptable |
| 0.125 | uncoated | 7 | 0 | acceptable |
|  | surfactant coated | 7 | 0 | acceptable |
| 0.250 | uncoated | 7 | 0 | acceptable |
|  | surfactant coated | 6 | 0 | acceptable |
| 0.625 | uncoated | 6 | 0 | acceptable |
|  | surfactant coated | 6–7 | 0 | unacceptable |

[1] The number of tests out of a total of 16 giving incomplete signal, that is, incomplete dye formation on the membrane due to inadequate spreading. Only a 0 score is acceptable.
[2] ZONYL TM FSN coverage on the membrane was 0.05 g/m².

The data indicate the following:

(1) considering all the parameters, that is, visual scores of dye density, number of incomplete signals and spot quality, the acceptable concentration of ZONYL TM FSN in the buffered composition on the surfactant coated membranes is greater than about 0.025 and less than about 0.625 weight %. The preferred range is from about 0.1 to about 0.5 weight %. A more preferred range is from about 0.1 to about 0.25 weight %, particularly when the membrane is uncoated.

(2) The 0.125 weight % concentration of ZONYL TM FSN on the surfactant coated membrane is especially preferred, since that amount adequately wets the membrane, and provides good visual scores, no incomplete signals and uniform spot quality. Also, at this concentration, one can use a wide range of volumes for integration into the positive control well, such as from about 5 μl to about 30 μl.

(3) BIODYNE TM A membranes, uncoated or coated with ZONYL TM FSN are useful. However, the coated membrane is superior when used with low surfactant compositions in the buffered composition.

The invention has been described in detail with particular reference to preferred embodiments thereof, but it will be understood that variations and modifications can be effected within the spirit and scope of the invention.

We claim:

1. A buffered composition comprising whole chlamydial or gonococcal organisms or an extracted antigen thereof, a protein, a preservative, a water-soluble fluorescent dye, and a nonionic fluorinated surfactant in an amount of at least about 0.05 weight percent.

2. The composition of claim 1 comprising extracted chlamydial or gonococcal antigen.

3. The composition of claim 1 buffered to a pH of from about 6 to about 9.

4. The composition of claim 1 wherein said surfactant is a perfluoroalkylpolyoxyethylene derivative having from 8 to 14 oxyethylene groups and from 3 to 8 perfluoroalkyl groups.

5. The composition of claim 1 wherein said nonionic surfactant is present in an amount of from about 0.1 to about 0.5 weight percent.

6. An article comprising a water-insoluble substrate having coated thereon a buffered composition comprising whole chlamydial or gonococcal organisms or an extracted antigen thereof, a protein, a preservative, a water-soluble fluorescent dye, and a nonionic fluorinated surfactant in an amount of at least about 0.5 weight percent.

7. The article of claim 6 which is a diagnostic test device having at least two test wells, one of which has said composition coated therein.

8. The article of claim 7 wherein each test well has a nonionic polyamide microporous membrane at the bottom thereof.

9. The article of claim 6 wherein said surfactant is a perfluoroalkylpolyoxyethylene derivative having from 8 to 14 oxyethylene groups and from 3 to 8 perfluoroalkyl groups.

10. The article of claim 6 wherein said coating comprises extracted chlamydial or gonococcal antigen.

11. A disposable test device comprising a water-insoluble shell and disposed within that shell three test wells, each having a nonionic polyamide microporous membrane at the bottom thereof, and one of said test wells having coated on the membrane therein a buffered composition comprising extracted chlamydial or gonococcal antigen, a protein, a preservative, a water-soluble fluorescent dye and a nonionic fluorinated surfactant in an amount of at least about 0.05 weight percent.

12. The test device of claim 11 wherein said coated composition comprises a perfluoroalkylpolyoxyethylene nonionic surfactant having from 8 to 14 oxyethylene groups and from 3 to 8 perfluoroalkyl groups, said surfactant present in an amount of from about 0.1 to about 0.5 weight percent.

13. A method for the determination of a chlamydial or gonococcal antigen in a biological specimen carried out in a disposable test device while simultaneously providing a positive control test, said test device having a first test well being suited for the determination of the unknown antigen, and a second test well being suited as a positive control by having coated therein a buffered composition comprising a mixture of whole chlamydial or gonococcal organisms or an extracted antigen thereof as control antigen, respectively, and a nonionic fluorinated surfactant in an amount of at least about 0.05 weight percent, each of said test wells having a nonionic polyamide microporous membrane located at the bottom thereof, said method comprising the steps of:

A. adding an aqueous solution containing unknown amounts of a chlamydial or gonococcal antigen extracted from a biological specimen suspected of containing chlamydial or gonococcal organisms, respectively, to said first and second test wells, to bind both unknown and control antigen to the respective membranes in said first and second test wells, B. contacting chlamydial or gonococcal antigen bound to said membrane in each test well with chlamydial or gonococcal antibody, respectively, so as to form an immunological complex on each of said membranes, and C. detecting the presence of complex on the membrane in said first test well as an indication of the presence of unknown chlamydial or gonococcal organisms in said biological specimen, and detecting the presence of complex on the membrane in said second test well as a positive control, the complexes being detected from a signal provided by either:

(1) a label on said chlamydial or gonococcal antibody, or (2) unlabeled chlamydial or gonococcal antibody, and a labeled antibody specific to said unlabeled chlamydial or gonococcal antibody.

14. The test device of claim 11 containing a third test well being suited as a negative control, said third test well containing a negative control reagent containing no antibodies specific to either said chlamydial or gonococcal antigen.

15. The method of claim 13 for the determination of the chlamydial lipopolysaccharide.

16. The method of claim 13 wherein said label is an enzyme, and complex determination is accomplished by contacting said enzyme with a composition which provides a dye in the presence of said enzyme.

17. The method of claim 13 wherein said buffered composition is coated on the membrane of said second test well.

18. The method of claim 13 wherein said surfactant is a perfluoroalkylpolyoxyethylene derivative having from 8 to 14 oxyethylene groups and from 3 to 8 perfluoroalkyl groups, which is present in said coating in an amount of from about 0.1 to about 0.5 weight percent.

* * * * *